United States Patent [19]

Scherberg

[11] 4,383,033

[45] May 10, 1983

[54] RADIOIODINE LABELING DURING PROTEIN SYNTHESIS

[75] Inventor: Neal H. Scherberg, Chicago, Ill.

[73] Assignee: University Patents, Inc., Norwalk, Conn.

[21] Appl. No.: 207,516

[22] Filed: Nov. 17, 1980

Related U.S. Application Data

[62] Division of Ser. No. 21,103, Mar. 16, 1979, Pat. No. 4,260,737.

[51] Int. Cl.$^3$ .................. C12P 21/00; C12P 21/02; C12N 1/00
[52] U.S. Cl. ............................ 435/68; 435/70; 435/317; 536/27
[58] Field of Search .................. 435/68, 317, 70

[56] References Cited

PUBLICATIONS

Scherberg et al.; J. Biol. Chem. 253, 1773 (1978).
Pelham et al., Eur. J. Biochem. 67, 247 (1976).
Clark et al., Methods Enzymol. 30 F, 754 (1974).
Brown et al., Biochim. Biophys. Acta 148, 423 (1967).
Woodward et al., Methods Enzymol. 30 F, 740 (1974).
Cartouzou et al.; Biochem. Biophys. Res. Comm. 15, 82 (1964).

*Primary Examiner*—Alvin E. Tanenholtz
*Assistant Examiner*—James Martinell
*Attorney, Agent, or Firm*—Jerome M. Teplitz

[57] ABSTRACT

Radioiodination of aminoacyl-transfer RNAs with either $^{125}I$ or $^{131}I$ resulted in the preferential addition of radioiodine to bound tyrosine. The radioiodinated tyrosyl-tRNA was 10-fold purified by chromatography and was found to consist essentially of monoiodo- and diiodo-tRNA in approximately equal isotopic proportions. The radioiodinated tyrosine was readily incorporated into proteins synthesized in broken cell reactions.

The specific activity of the iodine-labeled proteins can be modulated up to the highest theoretical value (radioiodine in each tyrosine) yielding products that are valuable for use in immunoassay procedures in research and in the determination of proteins of clinical importance. In addition to the mature proteins (processed by natural post-synthetic reactions) the product proteins can comprise prohormone-type molecules which represent the precursor of normal circulating forms of hormones. The $^{125}I$-protein, -hormone, or -prohormone can be employed advantageously in diagnosis to provide marker compounds for chromatographic detection, immunoprecipitation, and serum clearance testing.

3 Claims, No Drawings

RADIOIODINE LABELING DURING PROTEIN SYNTHESIS

The invention described herein was made in the course of work under a grant or award from the Department of Health, Education, and Welfare.

This application is a division of my prior U.S. application Ser. No. 021,103, filed Mar. 16, 1979, now U.S. Pat. No. 4,260,737, issued Apr. 7, 1981.

This invention relates to radioiodine labeling during protein synthesis and to the use of such labeled proteins as marker compounds in analysis of physiological processes. In one aspect, this invention relates to the preparation of the isotopic radioiodinated tyrosyl-transfer RNAs, namely $^{125}$I-tyr-tRNA and $^{131}$I-tyr-tRNA. In another aspect, this invention relates to the use of such radioiodine labeled tyr-tRNA as a precursor in the synthesis of labeled proteins that are useful in chromatographic detection, immunoassay, immunoprecipitation, and serum testing procedures.

Direct iodination of protein is known in the art. Iodine isotopes are readily introduced into purified protein by chemical or enzymatic means. The procedure of this invention is distinguishable over prior art methods in three important aspects:

(1) The radioiodine labeled protein formed can be obtained unmodified by post-synthetic events such as addition of sugar residues, specific cleavage of the polypeptide chain, or reassociation into specific combinations of peptide chains. The types and extent of such modification of the protein formed in the presence of the iodine isotopic precursor depend upon the type of broken cell preparation used. Thus, whereas chemical or enzymatic radioiodination is carried out with mature, fully modified protein as isolated from tissue or serum, the iodine labeling in the process of this invention occurs during synthesis before the aforementioned modifications. The protein so produced can be significantly different from those prepared by prior art methods, but it can possess overlapping immunological characteristics.

(2) In chemical or enzymatic labeling of proteins, the structure of the mature protein plays a limiting role in respect to the number and specific sites that can add iodine. Some tyrosyl residues, buried within the molecular configuration, can be poorly- or non-reactive. This has the effect of limiting the specific radioactivity of the product and in some instances can prohibit labeling without resort to complex chemical additions. Moreover, where more vigorous chemical conditions are utilized, or even in commonly employed standard reaction conditions, denaturation or modification of the protein of interest can occur. By contrast, in the method of this invention, every tyrosyl group has an equal chance of including radioiodine, and deleterious modifications due to incompatible buffer solutions or to oxidizing conditions are excluded.

(3) Prior art chemical or enzymatic radioiodination methods are not useful for the measurement of protein synthesis since such methods presuppose the existence of a preformed protein.

Accordingly, it is an object of this invention to minimize or eliminate the above-mentioned limitations of the prior art.

It is another object of this invention to provide a method for preparing a new class of radioiodine labeled protein, namely the immature, unmodified, newly synthesized proteins.

It is a further object to provide a method for radiolabeling of protein during protein synthesis for the purpose of quantification and qualitative investigations.

It is still another object to provide precursor radioiodine-tyr-tRNA for the production of marker proteins for use in bioanalytical procedures.

These and other objects will become apparent as the description of the invention proceeds.

In accordance with this invention, a buffered mixture of aminoacyl-tRNAs and sodium radioiodine is formed and the iodination reaction is initiated by the addition of Chloramine-T. Iodination is essentially completed after an incubation period of a few minutes at room temperature, whereupon the radioiodinated aminoacyl-tRNA fraction is isolated, suitably by chromatographic procedures. In consequence of this reaction, preferential iodination of bound tyrosine occurred, yielding a mixture of radioactive monoiodo- and diiodo-tyrosyl-tRNAs in approximately equal proportions.

Addition of the iodine-labeled tyr-tRNAs to a rabbit reticulocyte lysate resulted in the incorporation of iodinated tyrosine into protein. In a lysate coded by rat pituitary RNA, the iodinated precursor was incorporated into a protein identical with rat prolactin or its prohormone, as determined by immunoprecipitation and electrophoresis. Upon proteolytic digestion of the immunoprecipitate, nearly 90% of the monoiodo- and diiodo-tyrosine was recovered. The incorporation into specific products in broken-cell translation was increased 19-fold by pretreatment of the lysate with micrococcal nuclease. In the nuclease treated lysate coded with pituitary or thyroid RNA, iodinated precursor was incorporated into protein precipitated with antisera to rat growth hormone or rat thyroglobulin.

Additional details of the procedure described above for the radio-iodination of aminoacyl-tRNAs are given in N. Scherberg, et al., Journal of Biological Chemistry 253, 1773–1779 (1978).

PREFERRED EMBODIMENTS OF THE INVENTION

The invention can be more readily understood and illustrated by reference to the following procedures and working examples.

Preparation of Aminoacyl-tRNAs

Aminoacyl-tRNAs were isolated from the livers of individual male Sprague Dawley rats maintained on a normal diet. Fresh liver was homogenized in a solution containing 0.35 M sucrose, 0.004 M magnesium acetate, 0.025 M potassium chloride, 0.001 M L-tyrosine at a ratio of 2 g of tissue per 50 ml. The suspension was centrifuged for 30 minutes at 35,000 X g and the supernatant liquid combined with 10 ml of 1.0 M sodium acetate (pH 5), then extracted three times with 40 ml of a mixture of phenol and chloroform. The RNA was collected by precipitation with ethanol, washed by reprecipitation and dissolved in 0.4 ml of 0.0125 M sodium acetate (pH 5.0), and passed across a Sephadex G-100 column (0.8×27 cm) pre-equilibrated with 0.1 M potassium acetate (pH 4.6). Elution was monitored as OD 260 mu and the second peak to emerge was adsorbed directly to a DEAE cellulose column (4×0.5 cm 0.9 meq/g). The column was washed with 1 ml portions of a buffer containing 0.3 M lithium chloride and 0.05 M potassium acetate (pH 4.6) to a constant base line absorbancy at 260 mu. Aminoacyl-tRNAs were eluted by increasing the lithium chloride concentration to 1.0 M. Recovery of the tRNA fraction was 0.4 mg/2 g of starting tissue. The isolate was stored at −20° C. as a suspension with 2 volumes of ethanol containing 0.01 sodium acetate (pH 5.0).

Radioiodination and Separation of Iodotyrosyl-tRNA

A reaction mixture was formed containing 0.2 ml of aminoacyl-tRNA (50 to 200 µg), 0.1 ml of 0.2 M sodium phosphate (pH 7.5), and 0.5 to 1.4 mCi carrier-free sodium $^{125}$I. The reaction was started by the addition of 0.002 ml of 8mg/ml Chloramine-T. After incubation for 5 minutes at 25° C., 0.005 ml of 0.1 M sodium bisulfite was added and the labeled tRNA fraction was separated by filtration through a Sephadex G-50 column (0.8×25 cm) pre-equilibrated and washed with 0.1 M sodium chloride, 0.1 M sodium acetate (pH 5.0). The initial peak was adsorbed immediately to a 4×0.5 cm benzoylated DEAE (BD)-cellulose column which was subsequently washed with 20 ml of a lithium chloride gradient (0.3 to 1.2 M) containing 0.005 M magnesium acetate, 0.02 M potassium acetate buffer (pH 4.6). The elution pattern of isotope had an early peak coincident with free iodine and two additional peaks. The isotope-containing substance in the second of the late peaks contains the $^{125}$I-tyrosyl-tRNA. In routine preparation, the elution is interrupted after emergence of the second peak, and the $^{125}$I-aminoacyl-tRNAs are eluted by purging the column with 1 ml aliquots of the buffer containing 1.2 M lithium chloride and 20% ethanol. For storage, the eluates were mixed with two volumes of ethanol, 0.01 M sodium acetate (pH 5.0) and held at −20° C.

It is understood that the procedure described above can be carried out with sodium $^{131}$I to provide $^{131}$I-tyrosyl-tRNAs.

Protein Synthesis

Translation in the rabbit reticulocyte lysate was carried out employing the standard reaction mixture containing 0.075 M potassium chloride, 0.002 M magnesium chloride, 0.01 Hepes (pH 7.5), 0.015 M creatine phosphate, 10 l of creatine phosphokinase, 0.1 mM ATP, 0.02 mM GTP, and specified amounts of labeled precursor and coding RNA. Reactions were started by final addition of rabbit reticulocyte lysate, which can be pretreated with nuclease, in a ratio resulting in a 2.5-fold dilution of the stock lysate. Incorporation of the $^{125}$I-tyrosyl residue from the labeled precursor is also catalysed by tissue homogenates of rat liver, rat pituitary, and wheat germ fraction reconstituted for protein synthesis. Thus the $^{125}$I-labeled precursor prepared from rat liver is compatible for application with cell homogenates from different tissues, species, and phyla.

Incorporation of the $^{125}$I-tyrosine from acylated-tRNA into specific protein was shown by the following experiment. A lysate system was coded with rat pituitary in a translation mixture containing both $^{3}$H-leucine and $^{125}$I-aminoacyl-tRNA. The product separated by the double antibody precipitation method was subjected to electrophoresis. Both isotopes were limited to a single coincident peak which migrated at or near the position of a marker $^{125}$I-labeled rat prolactin run simultaneously in a separate gel. When a similar $^{125}$I-labeled prolactin immuno-precipitate was digested with proteolytic enzymes the radioiodine-labeled compounds migrated coincidently with monoiodo-tyrosine and diiodo-tyrosine.

From the above-described experimental procedures and results, it is clear that the present invention provides a novel method for introducing radioiodine labeled tyrosine into newly synthesized protein. The availability of radioiodine-labeled tyrosyl-tRNA, according to the method of this invention, makes it possible to prepare radiolabeled standards for the development of new assay kits for the measurement of specific peptides, for example prohormones not readily purified for the purpose of chemical or enzymatic radioiodination. In this method, radiolabeling of the polypeptide of interest occurs prior to purification. Amounts of tissue as small as a few mgs can be used as starting material for the isolation of the desired iodine-labeled protein; the labeled precursor need only be added to a homogenate of the tissue followed by isolation of the specific protein by appropriate steps. Such a methodology is applicable to the preparation of specific radioiodine-labeled protein for the inclusion in kits useful for the analytic determination of such proteins by competitive binding or immunoassay.

The availability of both $^{125}$I-tyrosyl-tRNA and $^{131}$I-tyrosyl-tRNA, according to the method of this invention, makes possible a double labeling procedure in which each isotope is employed separately to label proteins directly by coding information of independent messenger RNAs. The products of the separate reactions can be combined and then characterized by electrophoresis to separate the variety of products. Difference in the original coding information can be detected by determination of the ratios of the two isotopes in different fractions. The numerous applications in which this method would be useful include analysis of messenger RNA in tissue responding to hormone treatment, detection of foreign coding RNA such as viral infection, and an analysis of the development program in embryos.

This invention has been disclosed in detail with particular reference to certain preferred embodiments thereof, but it is understood that variations and modifications can be effected within the spirit and scope of the appended claims. It is intended that all material contained in the above description be interpreted in an illustrative and not in a limiting sense.

What is claimed is:

1. A process for the broken-cell synthesis of protein containing radioiodo-tyrosine comprising the steps of:
   (a) forming a mixture comprising broken-cell lysate, messenger RNA, and radioiodo-tyrosyl-tRNA in a buffered solution;
   (b) incubating the mixture at a temperature and for a time sufficient to effect protein synthesis; and
   (c) terminating the synthesis by addition of RNase.

2. The process of claim 1 wherein the buffer solution provides a pH of about 7.5, the RNase is pancreatic RNase, and the radioiodo-tyrosyl-tRNA is selected from the group consisting of mono$^{125}$I-tyrosyl-tRNA, di$^{125}$I-tyrosyl-tRNA, mono$^{131}$I-tyrosyl-tRNA, and di$^{131}$I-tyrosyl-tRNA.

3. The process of claim 1, wherein said lysate has been subjected to a pretreatment with micrococcal nuclease.

* * * * *